United States Patent [19]

Morris et al.

[11] Patent Number: 4,591,272

[45] Date of Patent: May 27, 1986

[54] PHOTOTHERMAL DEFLECTION DENSITOMETER FOR THIN LAYER CHROMATOGRAPHY

[75] Inventors: Michael D. Morris; Tsuey I. Chen, both of Ann Arbor, Mich.

[73] Assignee: Board of Regents acting on behalf of University of Michigan, Ann Arbor, Mich.

[21] Appl. No.: 565,349

[22] Filed: Dec. 27, 1983

[51] Int. Cl.$^4$ .......................... G01J 3/42; G01N 21/41
[52] U.S. Cl. ..................................... 356/432; 356/344; 374/45; 374/124
[58] Field of Search ...................... 374/124, 45, 6, 5, 7, 374/117; 356/432, 444, 129

[56] References Cited

U.S. PATENT DOCUMENTS

| | | | |
|---|---|---|---|
| 4,150,899 | 4/1979 | Nakamura | 356/444 |
| 4,197,012 | 4/1980 | Kerenyi et al. | 356/444 X |
| 4,243,327 | 1/1981 | Frosch et al. | 356/432 |
| 4,299,494 | 11/1981 | Badoz et al. | 356/432 |
| 4,468,136 | 8/1984 | Murphy et al. | 356/432 X |

OTHER PUBLICATIONS

"Laser–Based Ultrasensitive Spectroscopy and Detection V.", R. A. Keller (Editor) of Proceedings of SPIE, vol. 426, Aug. 23–24, 1983, pp. 116–120.
"A Sensitive Photothermal Deflection Technique for Measuring Absorption in Optically Thin Media", A. C. Bocara et al, Applied Physics & Laser Spectroscopy Gp, pp. 1–11, 4/1980.
IBM Technical Disclosure Bulletin, vol. 21, No. 10, 3/1979. "Trace Analysis in Gases-Technique", Hermann et al, pp. 4208–4209.
Solid State Technology/Mar. 1982, "Thermal Wave Microscopy", pp. 91–97 (A. Rosencwarg).

Primary Examiner—Daniel M. Yasich
Attorney, Agent, or Firm—Head, Johnson & Stevenson

[57] ABSTRACT

A photothermal deflection detector for thin layer chromatography includes a translation means for holding and moving a thin layer chromatographic plate; a first impinging laser beam (e.g., 20 mW chopped argon laser) focused on the moveable thin layer chromatographic plate; a second probing laser beam (e.g., 2 mW He-Ne laser) intersecting the impinging laser beam directly above and parallel to the moveable thin layer chromatographic plate; and a laser deflection measuring means (e.g., knife edge, photodiode detector and lock-in amplifier demodulator) responsive to the thermal lens effect created by the absorption of the impinging laser beam by the separated compounds on the thin layer chromatographic plate. Such a system when applied to separated compounds (e.g., 1,2-napthaquinone, phenanthrenequinone and α-ionone) exhibits detection limits that range from 30 ng to 7.5 pg, depending upon the compounds's ability to absorb the impinging light.

7 Claims, 4 Drawing Figures

PHOTOTHERMAL DEFLECTION DENSITOMETER FOR THIN LAYER CHROMATOGRAPHY

The United States Government may have rights in this invention pursuant to research grant GM28484 awarded by the National Institutes of Health.

BACKGROUND OF THE INVENTION

1. Field of the Invention

This invention relates to a method and apparatus utilizing the photothermal deflection effect to measure light absorption on a thin layer chromatographic plate. More specifically, the invention relates to the use of a pair of intersecting laser beams, one impinging on and the other parallel to the chromatographic plate, for quantitative determination of the chromatographically resolved compounds (thin layer, electrophoresis, etc.).

2. Description of the Prior Art

Thin layer chromatograph (TLC) is generally acknowledged as a simple, rapid and versatile separation technique. In recent years, TLC technology has benefitted from the introduction of "high performance" plates, coated with very uniform layers of 5 to 10μ diameter silica. However, this high performance thin layer chromatography (HPTLC) requires both improved sample introduction techniques and improved detections systems. For example, in conventional thin layer chromatography, developed spot sizes are usually 5 to 6 mm in diameter. However, in HPTLC the spot size is only 1 to 2 mm in diameter and further reduction in spot size is possible. Consequently, the need still exists for detectors which can probe areas of approximately one square millimeter or less and still meet or exceed the characteristics of known detection systems.

Although the principles of diffuse reflectance spectroscopy, perhaps the most popular TCL detection technology, are well known and available in commercial instruments, the limitations of this detection system are also well recognized. The detection limit for diffuse reflectance is typically in the low nanogram range and is to be considered for purposes of HPTLC as a relatively insensitive measurement technique. Fundamentally, the reason is that as the amount of compound present decreases, the reflected light approaches an upper limit. Thus, measurement of a small amount of material requires measuring the small difference between two large numbers. Fluorescence detection, the most common alternative to reflectance measurements, avoids this problem and is ten to one thousand times more sensitive than reflectance, depending on the compound. Thus detection limits are often in the 1 to 10 picogram range. However, fluorescence detection is limited to those compounds which fluoresce, or for which suitable fluorescent derivatives can be conveniently prepared, and only a small fraction of known compounds fluoresce. Photoacoustic spectroscopy (PAC) has been suggested as an alternative for detection of non-fluorescent compounds in TLC. Thus, it is known to place an open-ended PAS cell directly on a TLC plate as well as to use Fourier Transform infra-red (FTIR) PAS on the TLC plates with either gas-microphone or piezoeloctric transducer detection. The detection limit of photoacoustic spectroscopy on TLC plate has been reported to be in the range of low nanograms to high picograms.

In princple, the properties of lasers make them prime candidates for optical detectors in contemporary chromatographic applications. For example, laser induced fluorescence has been investigated as a high performance liguid chromatography detector system, but again the fact that most compounds are not fluorescent and have very low quantum efficiencies limits such applications. Recently, thermal lens spectroscopy has been proposed as an alternative to photoacoustic spectroscopy. In thermal lens spectroscopy the change in index of refraction of a sample caused by absorption of light and subsequent heat generation is measured. However, the conventional thermal lens technique is not directly applicable to opaque solids; but a thermal lens can be formed in a coupling gas, such as air over a solid sample, and then probed as the deflection of a low power laser. This technique is called photothermal deflection or the "mirage effect". Photothermal deflection has been used as the detection scheme for FTIR spectroscopy of solids, but to the best knowledge of the inventors the thermal lens or photothermal deflection effect, prior to the present invention, has never been employed in the quantitative determination of compounds separated on thin layer chromatographic plates.

SUMMARY OF THE INVENTION

In view of the need for more sensitive detectors particularly in HPTLC applications, we have discovered an improved photothermal deflection method for the quantitative analysis of compounds separated on a thin layer chromatogram comprising the steps of: (a) impinging a first laser beam on a thin layer chromatographic plate containing a sample resolved into separate compounds such that the compounds selectively absorb the impinging laser light and heat the gas phase directly above the point of laser impingement; (b) probing the gas phase directly above the point at which the first laser beam impinges on the thin layer chromatographic plate with a second laser beam, wherein the second probing laser beam is essentially parallel to the plate; (c) sensing and recording the deflection of the second probing laser beam caused by the heating of the gas phase at the point of impingement thus establishing the absorbance of the separated compound at the point of laser impingement; (d) shifting the point at which the first laser impinges on the chromatographic plate; and (e) repeating the above steps (a) through (d) thus determining the absorbance of the resolved separate compounds of the sample as a function of their respective positions on the thin layer chromatographic plate.

Further, according to the method of the present invention, the thin layer chromatographic plate is mounted on a translation stage and shifting of the point at which the first laser impinges is accomplished by moving the plate on this translation stage. Thus the improved apparatus of the present invention involves a photothermal deflection densitometer comprising: (a) a translation means for holding a thin layer chromatographic plate and moving the thin layer chromatographic plate under an impinging laser beam such that the laser beam sweeps parallel to the direction of development of the sample spots on the thin layer chromatographic plate and substantially the full length of the developed spots; (b) a first laser source with laser beam directed to impinge on a thin layer chromatographic plate being held in the translation means; (c) a second laser source with laser beam directed to probe the gas phase directly above the point of impingement of the first laser beam on a thin layer chromatographic plate being held in the translation means; and (d) a laser beam deflection measuring means for sensing and recording the deflection of the second laser beam probing the gas phase directly above the point of impingement of the first laser beam on a thin layer chromatographic plate being held in the translation means.

In one preferred embodiment the impinging laser beam is a modulated laser source with the modulated laser beam being directed at the thin layer chromatographic plate. The probing of the gas phase with the second laser beam and sensing and recording the deflection of the second probing laser beam is accomplished by use of a knife edge that splits the second laser beam before being directed to a photodiode detector with lock-in amplifier demodulator. A mechanically chopped argon laser can be used as the impinging laser source and a He-Ne laser for the probing source.

It is an object of the present invention to provide a device that uses the photothermal deflection effect to measure the small fractional light absorption associated with various compounds separated on a thin layer chromatographic plate. It is a further object to provide a simple yet highly sensitive device which readily allows for the quantitative measurement of the separated compounds. Fulfillment of these objects and the presence and fulfillment of other objects will be apparent upon complete reading of the specifications and claims taken in conjunction with the attached drawing.

DESCRIPTION OF THE PREFERRED EMBODIMENTS

Figure 1:
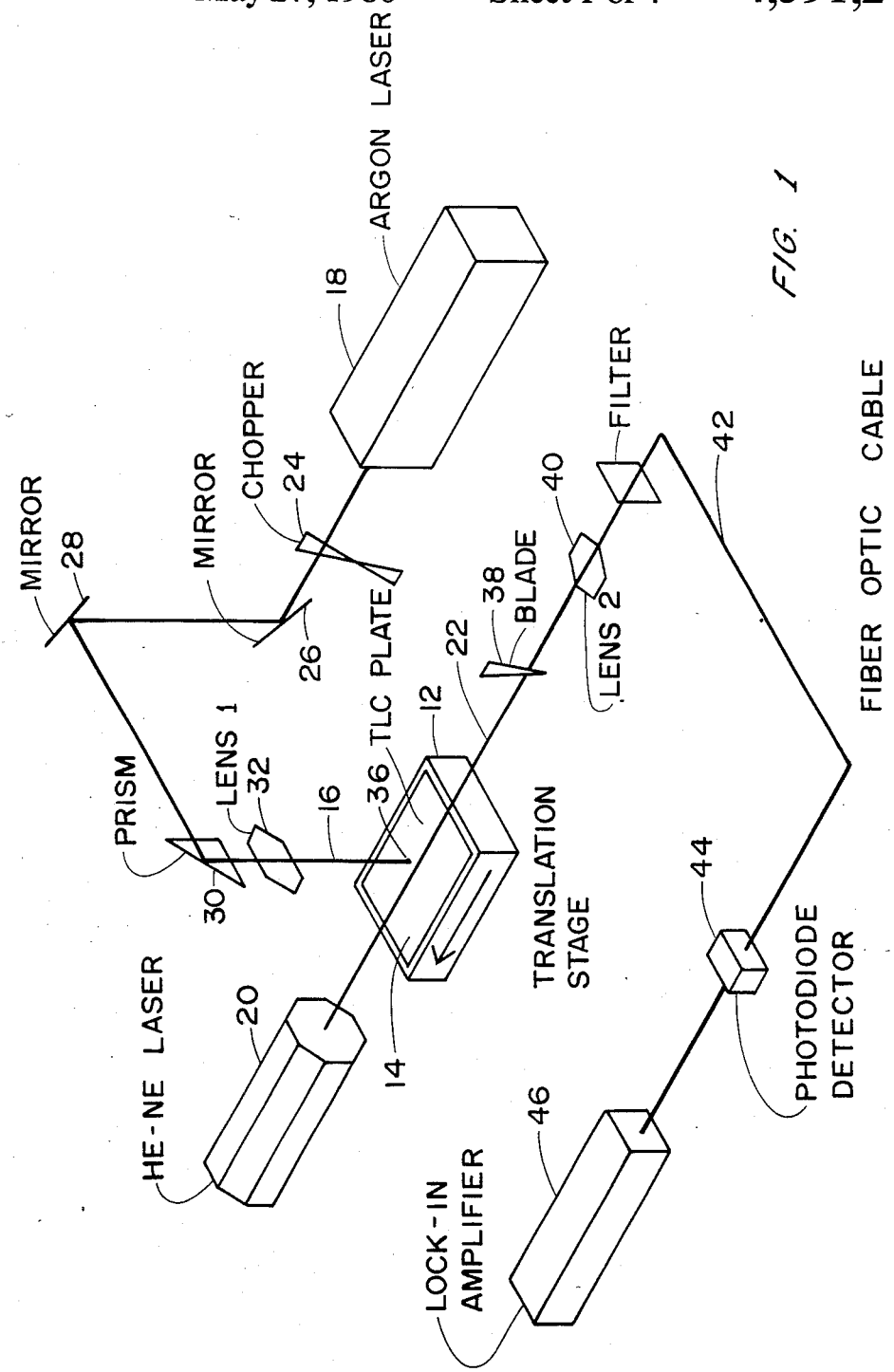
FIG. 1 illustrates, in a partial schematic representation, a photothermal deflection detector for thin layer chromatography according to the present invention.

The method and apparatus utilizing the photothermal deflection effect (or thermal lens effect) to measure small fractional light absorption by compounds separated on a thin layer chromatographic plate according to the present invention, how they differ from the prior art and the advantages of their use, can perhaps be best explained and understood by reference to the drawing. FIG. 1 schematically illustrates the overall photothermal deflection system, generally designated by the numeral 10. As illustrated, the system involves a translation stage 12 which is designed to hold a thin layer chromatographic (TLC) plate 14 and move the plate (as indicated by the arrow) such that the incident or impinging laser beam 16 originating from laser 18 sweeps essentially the entire length of the TLC plate 14. Behind the translation stage 12 is a second laser 20 with a probing laser beam 22 that is directed along the top surface of the TLC plate 14 in a direction (in this particular embodiment) parallel to the direction of development of the chromatographic spots (i.e., colinear to solvent and sample migration during separation).

As further illustrated in the specific embodiment of FIG. 1, the impinging laser source beam 16 is mechanically chopped 24 before being periscoped via mirrors 26 and 28 and prism 30 and aimed through focusing lens 32 onto the chromatographically resolved sample of TLC plate 14. The second laser beam 22 is carefully aligned to intersect the first laser beam 16 just above the surface of the TLC plate 14 such that the thermally induced change in refractive index of the air in contact with the TLC plate at the point of impingement 36 has maximum deflection effect (thermal lens effect) on the probing laser beam 16. After passing through the critical thermal lens region, the probing beam 16 passes across a conventional knife or razor edge 38, through a focus lens 40 to an optical fiber circuit 42. The optical fiber 42 leads to a photodiode detector 44 which is in communication (not shown) with the mechanical chopper 24 and which is used to demodulate the received photothermal deflection signal. The output from the lock-in amplifier can then be processed by conventional equipment including both digital and analog processing, recording on various media, and/or being displayed directly on various devices, all as well known in the art.

During use of the photothermal deflection densitometer illustrated in FIG. 1, a conventional TLC plate is fastened onto the translation stage and the translation stage is then driven such that the impinging laser beam scans the desired surface of the TLC plate. The amplifier output can then be analyzed as a function of position or distance along the TLC plate. In order to more fully illlustrate the specific concepts and features of the present invention the following examples are presented.

EXAMPLE I

A photothermal deflection system as illustrated in FIG. 1 was constructed using a 488.0 nm laser line from an argon ion laser (Coherent,Inc., CR-6) as the impinging light source. Stable operation of the laser could not be achieved at low power thus a power of 40 mW was maintained at the laser head and the laser beam was attenuated to 20 mW using a neutral density 0.3 filter. An aluminum mirrored periscope and right angle prism were used to aim the laser beam onto the sample. A 73 mm f.1 lens was used to loosely focus and control beam size. Reflection losses along the transmission optics train reduced the power to about 15 mW at the sample.

A mechanical chopper (Laser Precision, CTX-534) operated at 11 Hz was used to modulate the argon laser beam. A 2 mW He-Ne laser (Uniphase, 1103P) was used as the probe laser. A razor blade in the light path was used to detect beam deflection. The blade was fastened to a lens mount so that the fraction of the probe beam passed could be adjusted. The light passed by the blade focused (73 mm f.1 lens and 3-66 filter) into a 4 meter length of 400 $\mu$m diameter Pifax optical fiber to a photodiode (EG&G DT-25) located close to the remainder of the electronics. In order to avoid noise due to room air currents, the entire optical system from the prism to the fiber was enclosed in an aluminum case.

A lock-in amplifier (EG&G/PARC 5105) was used to demodulate the photothermal deflection signal. The output filter had a 1 second time constant and a 12 dB per octave attenuation. A small computer equipped with a 12 bit A/D converter was used to sample and store the lock-in amplifier output. The computer also performed peak height and area measurements and smoothing operations. A strip chart recorder was, on occasions, used to take data. The chromatogram was scanned by placing the plate on a translation stage driven by a motorized micrometer (Oriel). Provision was made to adjust the height of this stage to maximize the signal. With the system, a 50 mm length of plate could be scanned. Typically, scan speed was 11 mm/min.

EXAMPLE II

In order to test and evaluate the equipment and methods of the present invention, pre-coated 10 cm×10 cm HPTLC plates (Whatman) and test compounds α-ionone, phenanthrenequinone and 1,2-naphthaquinone (Aldrich) were obtained. The test compounds were initially diluted with acetone to about 10 mg/ml and stock solutions stored below 4° C. The stock solutions were further diluted with acetone just before use. Ceric sulfate prepared by adding 42 g of $(NH_4)_4Ce(SO_4)_4$ and 56 ml of conc. $H_2SO_4$ in 1 liter of distilled water was the chromogenic reagent.

Mixtures of the test compounmds were applied as 0.05 μl volumes with a 0.5 μl Hamilton microsyringe equipped with a no. 3 needle. The chromatograms were developed with a solvent system of benzene/ethyl acetate (5:1 v/v) 3 to 4 cm in a Regis SB/CD chamber. The plates were air dried and then placed on a hot plate at 86° C. for 2 to 3 minutes. As soon as the plates cooled to ambient temperature, they were sprayed with ceric sulfate and heated on a hot plate at 92° C. for 8 to 10 minutes. The HPTLC plates were scanned after they cooled to ambient temperature.

Utilizing the above procedure, solvent development was about 36 mm and the separation between spot centers was about 3-4 mm. Samples were applied as spots of less than 1 mm diameter. Development increased this to between 1 and 2 mm. $R_f$ values were 0.51 for 1,2-naphthaquinone, 0.63 for phenanthrenequinone and 0.71 for α-ionone. Ceric ion oxidation produced spots which were brown (1,2-naphthaquinone and α-ionone) or yellow (phenanthrenequinone).

Using the equipment and procedures in the Examples, the dependence of the signal to noise ratio on chopping frequency and on fraction of the probe beam passed by the razor blade was examined. It was found that although the signal decreased with increasing chopper frequency, the signal to noise ratio remained constant over the test region of 10 to 100 Hz. For this experiment a chopper frequency of 11 Hz was chosen.

Figure 2:
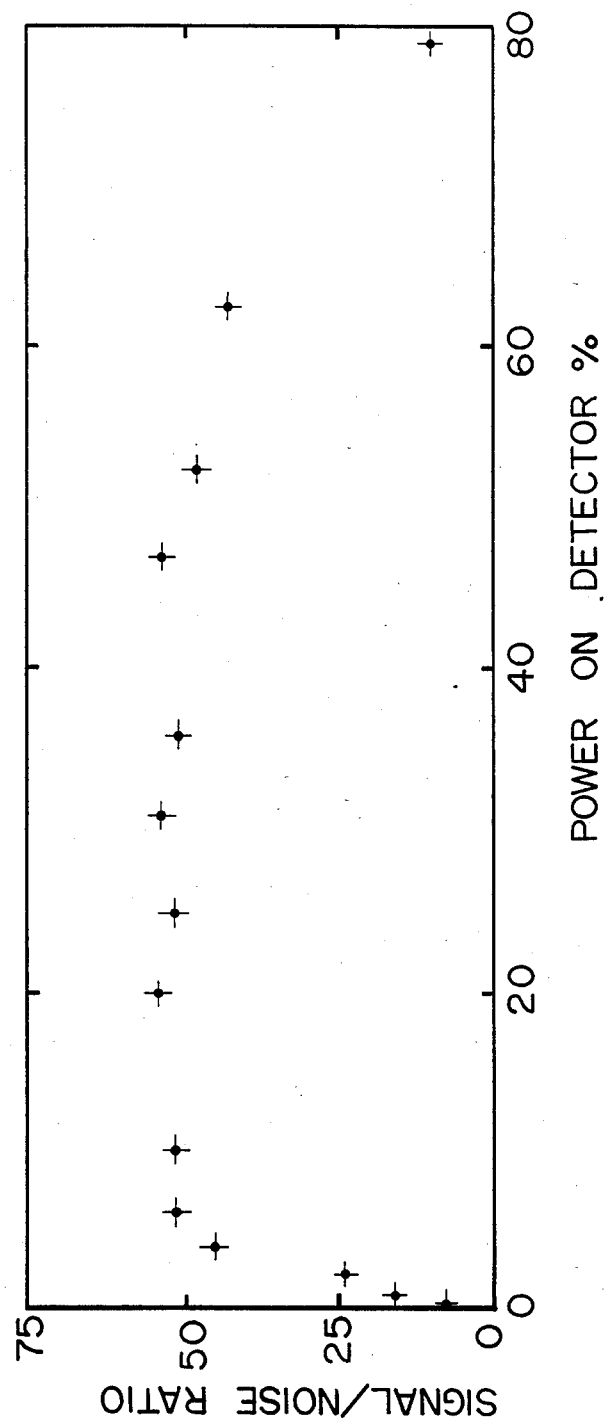
FIG. 2 is a plot of the signal to noise ratio as a function of the fraction of probe laser power received at the detector.

The plot of FIG. 2 illustrates the dependence of the signal to noise ratio on the fraction of the probe laser power passed by the razor blade. The signal to noise ratio maximizes over a very broad range, 6-45% passed. Thus, adjustment of the razor blade is not critical if an internal standard is used. Absolute measurements are satisfactory if the positions of the optical elements are fixed throughout a series of measurements.

Figure 3:
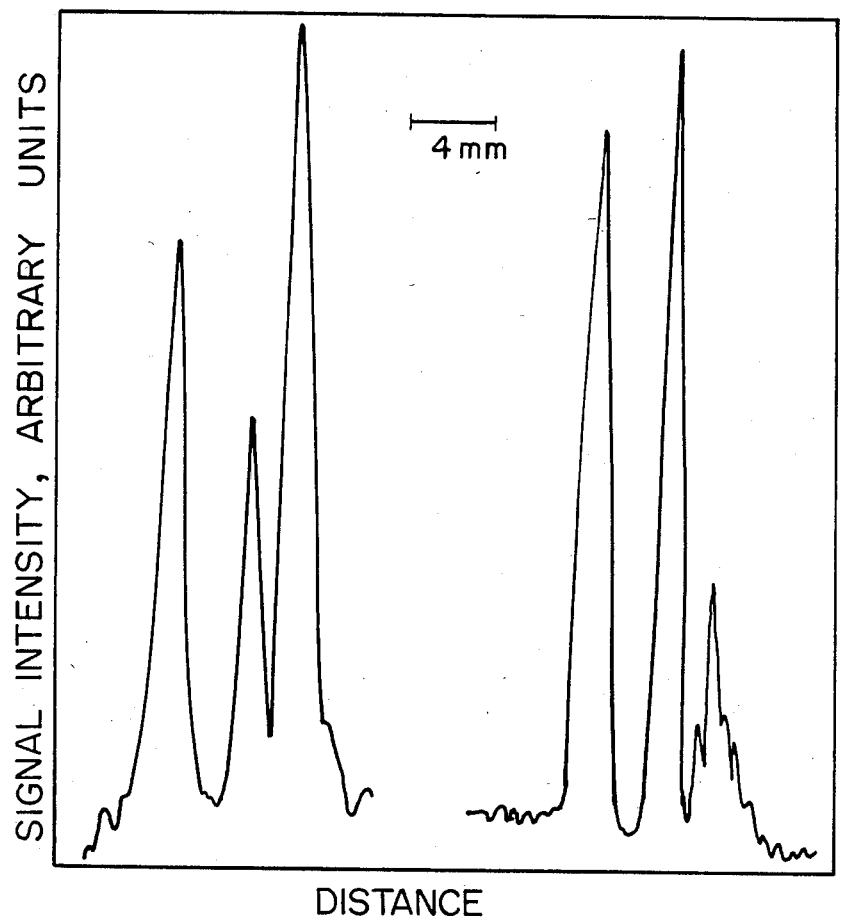
FIG. 3 illustrates a pair of typical chromatograms according to the present invention of two mixtures of the same condensed ring quinones at different relative quantities.

The photothermal deflection chromatograms for two mixtures of test compounds at varying relative quantities are shown in FIG. 3. The left chromatogram A represents a mixture of 144 ng 1,2-naphthaquinone, 93 ng phenanthrenequinone and 149 pg α-ionone. The right chromatogram B represents 144 ng 1,2-naphthaquinone, 186 ng phenanthrenequinone and 14.9 pg α-ionone. As illustrated chromatogram A shows all three compounds well above detection limits while in chromatogram B, the quantity of α-ionone is approaching the detection limits, and the peak is breaking up. The cause of the break-up of peaks at very low concentrations is uncertain, but may be due to irregularities in the coating of the TLC plate.

Figure 4:
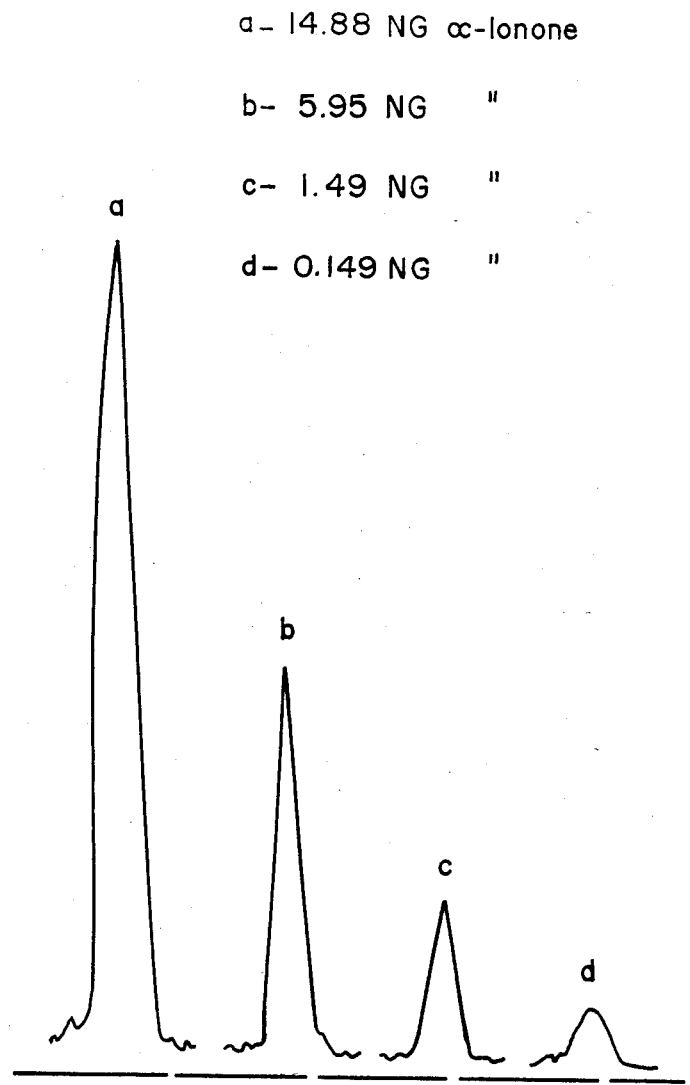
FIG. 4 illustrates a series of photothermal deflection scans and resulting chromatograms according to the present invention for four different quantities of $\alpha$-ionone.

FIG. 4 illustrates a series of four photothermal deflection chromatograms of α-ionone at 14.88 ng, 5.95 ng, 1.49 ng and 0.149 ng respectively. Peak areas are reproducible to about 2.5% and are linear in amount of analyte over almost two orders of magnitude. Negative deviations from linearity occur at high values of analyte. This deviation is expected, since the quantity measured is proportional to the percentage of the incident light absorbed and must reach a limit as the sample becomes more opaque. Detection limits for the three compounds tested are α-ionone, 7.5 pg; 1,2-naphthaquinone, 2.3 ng; and phenanthrenequinone, 31 ng. This disparity of three orders of magnitude arises because the laser line used is not really near an absorption maximum of the latter two compounds. Preferably a laser source near an absorption maximum is to be employed for maximum sensitivity. Preferably the detector is to be shielded from laboratory air currents. Noise levels are more than ten times greater when the apparatus is operated in the open air than when it is enclosed. However, no special vibration isolation is necessary. Successful operation of the system has been achieved on a wooden table and on a honeycomb optical table. The flexibility of a wooden table is undesirable, but any rigid metal base is adequate. Unlike conventional densitometry or fluorescence, photothermal deflection is not sensitive to scattered light.

Photothermal deflection and dual beam thermal lens systems operate best if both beams have approximately the same diameter. Preferably the argon ion laser beam is reduced in size to match the helium-neon beam. This approach requires only one lens but produces a detector which samples only a small fraction of the cross-section of the chromatographic spot. It is contemplated that the use of cylindrical lenses or prisms as beam expanders will produce a detector with a slit-like cross-section which approximates the ideal shape of a densitometer for thin layer chromatography.

It should be appreciated that various overall equipment selections, configurations and optical paths can be employed in the present invention and as such should be considered equivalent for purposes of this invention. Thus it is contemplated that the TLC plate (as well as multiple plates) can be installed in more than one orientation and moved in more than one direction. The laser beams (both impinging and probing) can assume other relative orientations to the TLC plate than that specifically illustrated and exemplified herein. For example, multiple impinging laser beams (with or without differing frequencies) and/or a laser beam fanned out over one or a plurality of TLC plates mounted on a single moveable translation stage can be employed. Further, more than one probing laser beam can be employed at the same time, particularly if a multiple frequency or variable frequency laser source is used.

The advantages and benefits of the photothermal deflection detection system for thin layer chromatography according to the present invention are considered numerous and significant. The photothermal deflection system has been shown to be a simple and sensitive method for the quantitative interpretation of thin layer chromatograms. The detector system is easy to align and stable for a long period of time. Only modest laser power is needed to reach picogram sensitivity and the system is operable with inexpensive lasers. The operability observed in the visible region should extend into other regions of the spectrum including the ultraviolet as well as being generally compatible with new laser sources such as excimer laser and various metal vapor lasers (copper ion or silver).

It is further contemplated that the impinging laser can be replaced with a pulsed laser. In this embodiment, gated integration rather than lock-in amplification is used to process the signal. The He-Ne laser can be replaced with any CW laser. A diode laser, suitably shaped with lenses would be a satisfactory alternative. The knife-edged/photodiode and most importantly, both the impinging laser and the probing laser can be fanned out across the plate, normal to the direction of scanning. If the single photodiode is replaced with an array of photodiodes, the entire plate can be scanned in a single pass, providing a ten to twenty fold decrease in time required to process a plate. It should be further appreciated that the thin layer chromatographic plate according the the present invention refers to any opaque substrate having a chromatographically separated sample thereon (e.g., thin layered solvent chormatography, electrophoresis and the like).

Having thus described the preferred embodiments with a certain degree of particularity, it is manifest that many changes can be made in the details of the invention without departing from the spirit and scope of the invention. Therefore, it is to be understood that the invention is not limited to the embodiments set forth herein for purposes of exemplification, but is to be limited only by the scope of the attached claims, including a full range of equivalents to which each element thereof is entitled.

We claim:

1. A photothermal deflection method for quantitative analysis of compounds separated on a thin layer chromatogram comprising the steps of:
   (a) impinging a first laser beam on a thin layer chromatographic plate containing a sample resolved into separate compounds such that said compounds selectively absorb said impinging laser light and heat the gas phase directly above the point of laser impingement;
   (b) probing the gas phase directly above said point at which said first laser beam impinges on said thin layer chromatographic plate with a second laser beam, wherein said second probing laser beam is essentially parallel to said plate;
   (c) sensing and recording the deflection of said second probing laser beam caused by the heating of said gas phase at said point of impingement thus establishing the absorbance of the separated compound at said point of laser impingement;
   (d) shifting the point at which said first laser impinges on said chromatographic plate; and
   (e) repeating the above steps (a) through (d) thus determining the absorbance of the resolved separate compounds of said sample as a function of their respective positions on said thin layer chromatographic plate.

2. A method of claim 1 wherein said thin layer chromatagraphic plate is mounted on a translation stage and said shifting of the point at which said first laser beam impinges is accomplished by translating or moving said thin layer chromatographic plate on said translation stage.

3. A method a claim 1 wherein said impinging of said first laser beam is accomplished by use of a modulated laser source with the modulated laser beam being directed at said thin layer chromatographic plate and said probing of said gas phase with said second laser beam and said sensing and recording the deflection of said second probing laser beam is accomplished by use of a knife edge that splits said second laser beam being directed to a photodiode detector with lock-in amplifier demodulator.

4. A method of claim 3 wherein said first laser beam is from a mechanically chopped argon laser source and said second laser beam is from a He-Ne laser source.

5. A photothermal deflection densitometer comprising:
   (a) a translation means for holding a thin layer chromatographic plate and moving said thin layer chromatographic plate under an impinging laser beam such that said laser beam sweeps parallel to the direction of development of the sample spots on said thin layer chromatographic plate and substantially the full length of said developed spots;
   (b) a first laser source with laser beam directed to impinge on a thin layer chromatographic plate being held in said translation means;
   (c) a second laser source with laser beam directed to probe the gas phase directly above said point of impingement of said first laser beam on a thin layer chromatographic plate being held in said translation means; and
   (d) a laser beam deflection measuring means for sensing and recording the deflection of said second laser beam probing said gas phase directly above said point of impingement of said first laser beam on a thin layer chromatographic plate being held in said translation means.

6. A photothermal deflection densitometer of claim 5 wherein said first laser source is a modulated laser source and said laser beam defletion measuring means is a knife edge that splits said second laser beam and a photodiode detector with lock-in amplifier demodulator.

7. A photothermal deflection densitometer of claim 6 wherein said modulated laser source is a mechanically chopped argon laser source and said second laser source is a He-Ne laser source.

* * * * *